United States Patent
Feldschuh

(10) Patent No.: US 11,801,002 B2
(45) Date of Patent: Oct. 31, 2023

(54) REMOTE BLOOD VOLUME MONITOR

(71) Applicant: DAXOR CORP., New York, NY (US)

(72) Inventor: Jonathan Feldschuh, Jackson Heights, NY (US)

(73) Assignee: DAXOR CORP., New York, NY (US)

( * ) Notice: Subject to any disclaimer, the term of this patent is extended or adjusted under 35 U.S.C. 154(b) by 786 days.

(21) Appl. No.: 16/823,482

(22) Filed: Mar. 19, 2020

(65) Prior Publication Data

US 2020/0297259 A1     Sep. 24, 2020

Related U.S. Application Data

(60) Provisional application No. 62/820,393, filed on Mar. 19, 2019.

(51) Int. Cl.

| | |
|---|---|
| *A61B 5/157* | (2006.01) |
| *A61B 5/0205* | (2006.01) |
| *A61B 5/00* | (2006.01) |
| *A61B 5/029* | (2006.01) |
| *A61B 5/0275* | (2006.01) |
| *A61B 5/145* | (2006.01) |
| *A61B 5/15* | (2006.01) |
| *A61B 5/024* | (2006.01) |
| *A61B 5/20* | (2006.01) |
| *A61B 5/02* | (2006.01) |
| *A61B 5/1455* | (2006.01) |
| *G16H 20/17* | (2018.01) |

(52) U.S. Cl.
CPC ............ *A61B 5/157* (2013.01); *A61B 5/0071* (2013.01); *A61B 5/0205* (2013.01); *A61B 5/029* (2013.01); *A61B 5/02042* (2013.01); *A61B 5/02416* (2013.01); *A61B 5/02755* (2013.01); *A61B 5/1455* (2013.01); *A61B 5/14532* (2013.01); *A61B 5/14535* (2013.01); *A61B 5/14542* (2013.01); *A61B 5/14546* (2013.01); *A61B 5/15003* (2013.01); *A61B 5/201* (2013.01); *A61B 5/412* (2013.01); *A61B 5/441* (2013.01); *A61B 5/742* (2013.01); *G16H 20/17* (2018.01)

(58) Field of Classification Search
CPC . A61B 5/14556; A61B 5/029; A61B 5/14532; A61B 5/14535; A61B 5/14542; A61B 5/14546; A61B 5/201; A61B 5/412; A61B 5/742; A61B 5/4836

See application file for complete search history.

(56) References Cited

U.S. PATENT DOCUMENTS

| | | | |
|---|---|---|---|
| 5,024,231 A | 6/1991 | Feldschuh et al. | |
| 8,246,546 B2 * | 8/2012 | Huiku | A61B 5/02028 600/483 |
| 9,002,656 B2 | 4/2015 | Feldschuh et al. | |
| 9,002,657 B2 | 4/2015 | Feldschuh et al. | |

(Continued)

FOREIGN PATENT DOCUMENTS

| | | |
|---|---|---|
| WO | 2021/222575 A1 | 11/2021 |
| WO | 2021/222594 A1 | 11/2021 |

*Primary Examiner* — Eric F Winakur
(74) *Attorney, Agent, or Firm* — Amster, Rothstein & Ebenstein LLP

(57) ABSTRACT

Systems and methods are disclosed for providing ongoing monitoring and updating of blood volume status, where the system or method can include guidance in the form of recommendations for treatment actions or alerts about altered patient status.

35 Claims, 5 Drawing Sheets

(56) References Cited

U.S. PATENT DOCUMENTS

| | | |
|---|---|---|
| 11,204,356 B2 | 12/2021 | Feldschuh et al. |
| 2007/0178167 A1* | 8/2007 | Andrijauskas ............ A61P 7/04 |
| | | 424/529 |
| 2008/0195023 A1 | 8/2008 | Feldschuh |
| 2013/0317322 A1* | 11/2013 | Andrijauskas ....... A61B 5/4875 |
| | | 600/309 |
| 2018/0217168 A1 | 8/2018 | Feldschuh et al. |
| 2019/0192060 A1 | 6/2019 | Hobbs et al. |
| 2020/0132668 A1 | 4/2020 | Feldschuh et al. |
| 2020/0132676 A1 | 4/2020 | Feldschuh |
| 2020/0132677 A1 | 4/2020 | Feldschuh et al. |

* cited by examiner

REMOTE BLOOD VOLUME MONITOR

CROSS-REFERENCE TO RELATED APPLICATIONS

This application claims the benefit of U.S. Provisional Patent Application No. 62/820,393, filed on Mar. 19, 2019, the contents of which are herein incorporated by reference in their entirety into the present application.

FIELD OF THE INVENTION

The present invention relates to medical diagnosis, monitoring and treatment of patients. Systems and methods are presented for remote monitoring of blood volume of a living creature, after an initial blood volume measurement has been made.

BACKGROUND OF THE INVENTION

Knowledge of blood volume is important in diagnosing and treating numerous medical conditions, including heart failure, hypertension, trauma, sepsis, acute respiratory distress syndrome (ARDS), syncope, and many others. A blood volume analyzer (BVA) is an instrument or system capable of measuring and reporting the volume of blood of a living being. The Daxor BVA-100 Blood Volume Analyzer, based on U.S. Pat. No. 5,024,231, is a commercially available, FDA-approved device. It operates on the indicator-dilution principle. I-131-labelled Human Serum Albumin (HSA) is injected into a patient's blood stream, and various samples of blood are taken at timed intervals after mixing has occurred. Other tracers have been employed to measure blood volume, including dyes such as Evans Blue, fluorescent compounds such as ICG, and other radioactive tracers such I-125 and Cr-51. These compounds have been used to label naturally occurring blood components (typically plasma proteins such as albumin or entire red blood cells), other molecules of various sizes which can safely be introduced into the bloodstream, or as a naked tracer. Regardless of the tracer and exact method used, the indicator-dilution technique presents challenges for both repeated measurements of blood volume status, and for ongoing monitoring of blood volume status. Some tracers (especially radioactive ones) may have cumulative exposure limits for patients that may make multiple measurements undesirable or impossible. Tracer clearance from the bloodstream is an important issue: a tracer that clears too slowly from the bloodstream will interfere with the accuracy of subsequent tests (even if background measurements are taken); a tracer that clears too quickly from the bloodstream may not provide accurate measurements of blood volume in the first place. Beyond issues related to the use of a tracer, there are also practical issues related to the performance of the method, namely that it is a relatively complex test that is performed in a hospital or clinical setting, by a technician who has received specialized training, and requires a specialized compound to be administered to the patient through an IV, and at least one sample of blood to be taken at a measured time interval. It would be beneficial to be able to monitor blood volume status much more conveniently. This improved convenience could be manifested as one or more of the following: capability for frequent or continuous monitoring of blood volume status; ability for follow-up testing to be performed by nurse or other medical professional with no specialized training, or by an individual (such as the patient) with no medical training. Such a more convenient follow-up test would almost certainly cost less to provide.

So-called "Relative Blood Volume Monitoring" using changes in Hct has been disclosed (for example by the Blood Volume Monitor for use during dialysis, as marketed by Fresenius) but such monitors have not incorporated the measurement of actual (i.e. absolute) blood volume. Without the knowledge of actual blood volume, any observed changes in Hct cannot be related to normal values for blood volume for a given patient, or indeed even to actual volumes of fluid (since the Hct only provides information about the relative proportions of fluid in the bloodstream).

The knowledge derived from frequent or continuous monitoring of blood volume status can be used to guide treatment for a patient, just as knowledge from an initial blood measurement can be used to guide treatment. Such guidance is the subject of U.S. patent application Ser. No. 16/667,945, "BLOOD VOLUME ANALYZER WITH GUIDANCE", filed Oct. 30, 2019. The disclosures of this publication are hereby incorporated by reference in their entirety into the subject application to more fully describe the art to which the subject invention pertains.

The knowledge derived from a blood volume measurement can shed light on other blood tests, for example by euvolemic correction of measured concentrations, as is discussed in US Patent Application 2018/0217168, "BLOOD VOLUME ANALYZER WITH VOLUME—AWARE BLOOD COMPONENT MEASURES", filed Jan. 29, 2018. The disclosures of this publication are hereby incorporated by reference in their entirety into the subject application to more fully describe the art to which the subject invention pertains.

SUMMARY OF EMBODIMENTS OF THE PRESENT INVENTION

The present invention discloses systems and methods for providing ongoing updating and monitoring of blood volume status. In some embodiments, the system or method also includes guidance, e.g. in the form of recommendations for treatment actions or alerts about altered patient status.

In one preferred embodiment, a system or method includes a blood volume analyzer capable of performing an initial blood volume evaluation, and of storing the results. Also included is a component for entering information about how the patient's red cell status is changing. Also included is a component for measuring patient Hct at subsequent times, and of communicating such measurements to the analyzer, which updates its results (including current patient values, as well as deviations from patient ideal values) in the form of an updated or continuously updated report.

In one preferred embodiment, the information about the patient's red cell status is entered manually by a user, and quantifies the volume of red cells that may have been added by transfusion, and/or that may have been lost to bleeding, or specifies that red cell volume has been stable.

In one preferred embodiment, the information about red cell additions is transmitted to the analyzer automatically by a component that both performs the transfusion of a known volume of red cells and communicates with the analyzer.

In one preferred embodiment, the information about blood loss is transmitted to the analyzer automatically by a component that both measures the loss of blood to bleeding, and communicates with the analyzer.

In one preferred embodiment, the component for measuring Hct is a remote monitor which communicates its reading of Hct to the analyzer (base unit), such that updated measurements, guidance and alerts are made available to medical personnel via the base unit, and/or to the patient via the remote monitor.

In various preferred embodiments, customized, patient-specific guidance is produced based on published protocols, and the values calculated in an updated blood volume measurement. Such guidance is used to treat specific conditions such as Heart Failure, Hypertension, etc.

In various other preferred embodiments, the component for measuring Hct is combined with one or more other monitoring devices for other medical information; the combination of monitors allows the other devices' data to be adjusted by knowledge of volume status, and to be taken into account in the guidance provided by the system.

DETAILED DESCRIPTION OF THE INVENTION

Figure 1:
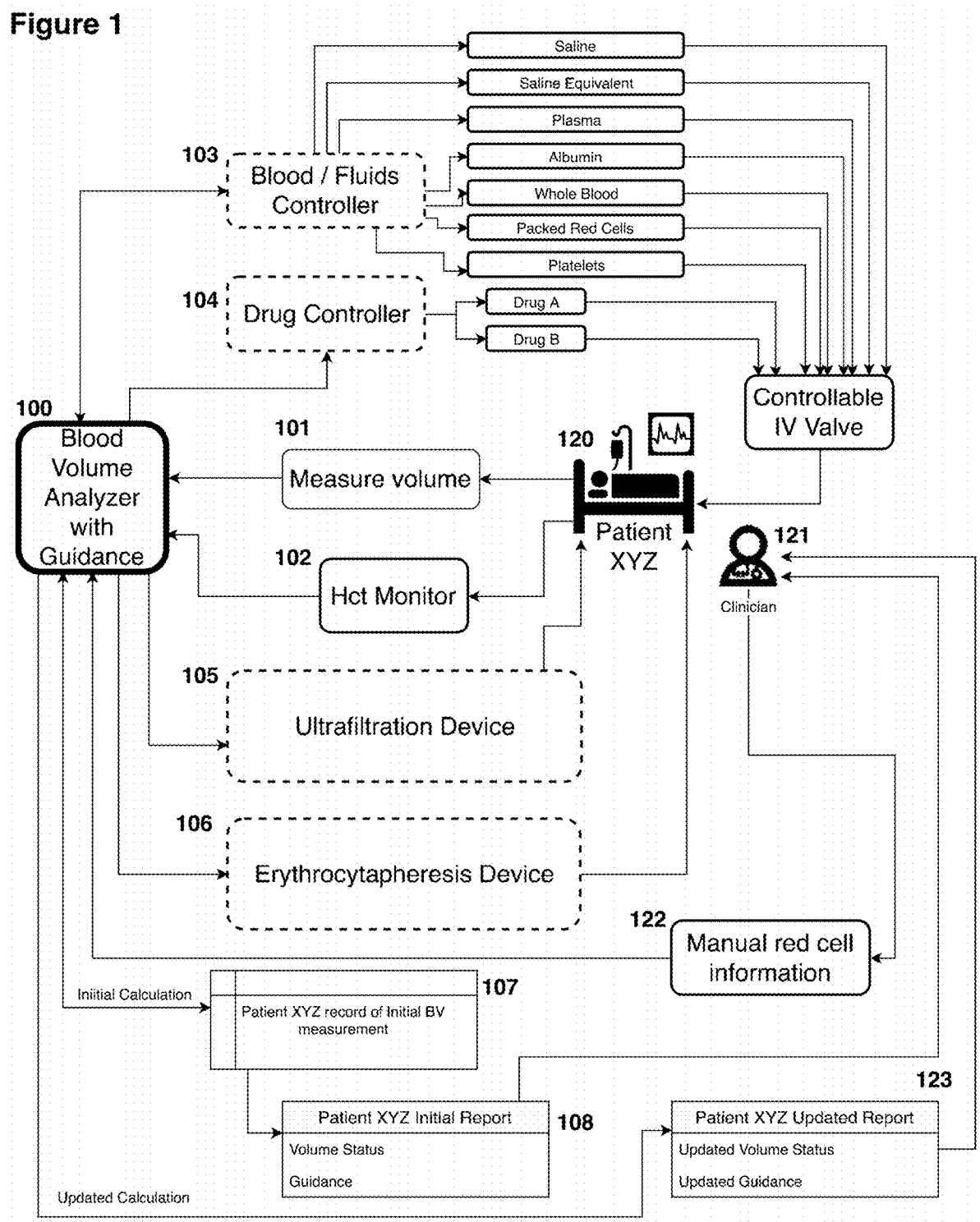
FIG. 1 shows a preferred embodiment of the system. A blood volume analyzer with guidance performs a volume measurement of patient XYZ. The analyzer produces an initial report of the patient's volume status, including guidance. A Hct monitor provides regular (or continuous) measurements of Hct, which are delivered to the analyzer. As Hct information and/or manual red cell information changes, an updated report is produced.

It is assumed that a Blood Volume Analysis is available for a patient, including values for the following quantities: Blood Volume (BV), Plasma Volume (PV), Red Cell Volume (RCV), and that normal values are also derived from knowledge of the patient's gender, height and weight: Ideal Blood Volume (iBV), Ideal Plasma Volume (iPV) and Ideal Red Cell Volume (iRCV). Such values can be derived by consulting the relationship described in "Prediction of the Normal Blood Volume" (Feldschuh et al, Circulation, vol. 56, No. 4, October 1977, pp. 605-612). In a preferred embodiment, all these values are taken from an automated Blood Volume Analyzer such as described in U.S. Pat. No. 5,024,231. This analyzer uses radio-labeled I-131. The contents of that patent are herein incorporated by reference. It is also assumed that a peripheral hematocrit (pHct) is available. In a preferred embodiment, these values are taken from a "Blood Volume Analyzer with Volume-Aware Blood Component Measures" such as described in U.S. Patent Application Publication No. US2018/0217168 A1. In another preferred embodiment, these values are taken from a "Blood Volume Analyzer with Guidance" such as described in U.S. patent application Ser. No. 16/667,945.

The overall whole body Hct (oHct) is related to the peripheral Hct by the following relationship:

$$oHct = pHct * paf \quad (1)$$

where $$paf = 0.9009 \quad (2).$$

This is due to the fact that blood cells are more concentrated in the peripheral circulation (from which blood samples are drawn) than the average value for the whole body; the constant paf is derived as the product 0.99*0.91, as described in U.S. Pat. No. 5,024,231, or a similar constant value. Red Cell Volume and Plasma volume are related to Blood Volume as follows:

$$BV = PV + RCV \quad (3)$$

$$RCV = BV * oHct = BV * pHct * paf \quad (4)$$

$$PV = BV * (1 - oHct) = BV * (1 - pHct * paf) \quad (5).$$

The Ideal Hct (iHct) is defined to be:

$$iHct \equiv \begin{cases} 0.45 \text{ for Males} \\ 0.40 \text{ for Females} \end{cases} \quad (6)$$

The Ideal Red Cell Volume (iRCV) and Ideal Plasma Volume (iPV) are calculated from the iBV. Note that the iHct is a peripheral Hct value, so the peripheral adjustment factor is required:

$$iBV = iPV + iRCV \quad (7)$$

$$iRCV = iBV * iHct * paf \quad (8)$$

$$iPV = iBV - iRCV = iBV * (1 - iHct * paf) \quad (9).$$

Guidance for treatment may be determined with reference to absolute deviations from ideal volumes, where the abbreviation "dev" is defined to be the deviation of a measured value from its respective Ideal value:

$$devBV = BV - iBV \quad (10)$$

$$devRCV = RCV - iRCV \quad (11)$$

$$devPV = PV - iPV \quad (12).$$

Guidance for treatment may also be determined with reference to percentage deviations from ideal volumes, where the abbreviation "edr" is defined to be the excess-deficit ratio of the deviation of a measured value from its respective Ideal value:

$$edrBV = \frac{devBV}{iBV} \quad (13)$$

$$edrRCV = \frac{devRCV}{iRCV} \quad (14)$$

$$edrPV = \frac{devPV}{iPV}. \quad (15)$$

This allows volume-aware metrics to be defined that incorporate actual and ideal volume measurements into a single ratio-like (i.e. unit-less) value.

After an initial measurement of Blood Volume status has been performed, it may be desirable to have an updated measurement, but without the inconvenience, effort, technical difficulties, etc. of performing subsequent direct measurements of BV using the indicator dilution method. The subscript "u" is used to indicate updated values, and "f" to indicate first (initial) values. The first measurement was performed at time $t_f$ and an updated measurement at time $t_u$. An updated peripheral Hct $pHct_u$ is obtained (e.g. using a subsequent blood draw and spun Hct, or via an inline monitor or other means). Consider a case in which we know that the RCV is unchanged. This will be the case, for example, if all of the following are true:
1) a relatively short time has elapsed since the first measurement (i.e. $t_u-t_f$ is relatively small), such that only negligible net production or destruction of red cells via internal processes is likely to have occurred
2) no bleeding has occurred
3) no blood products have been administered.

For this case $RCV_u=RCV_f$. Because of assumption 1) above, one can also assume that ideal volume values have remained constant, as these are calculated solely from patient gender, height, and weight. This implies that $iBV_u=iBV_f$, $iPV_u=iPV_f$, and $iRCV_u=iRCV_f$. Updated values are calculated as follows. Rewriting equations 4 and 5 to express BV and PV in terms of RCV:

$$BV = \frac{RCV}{pHct * paf} \quad (16)$$

$$PV = RCV * \frac{(1 - pHct * paf)}{pHct * paf} \quad (17)$$

Now using the assumption $$RCV_u = RCV_f \quad (18)$$

updated formulas for BV and PV are derived that depend only on an updated value for pHct.

$$BV_u = \frac{RCV_f}{pHct_u * paf} \quad (19)$$

$$PV_u = RCV_f * \frac{(1 - pHct_u * paf)}{pHct_u * paf} \quad (20)$$

Using the updated values, and noting that updated values for the ideal values are not required (as discussed above), one can also obtain updated deviations to use in generating guidance:

$$devBV_u = BV_u - iBV \quad (21)$$

$$devRCV_u = RCV_u - iRCV = devRCV_f \quad (22)$$

$$devPV_u = PV_u - iPV \quad (23)$$

And similarly:

$$edrBV_u = \frac{devBV_u}{iBV} \quad (24)$$

$$edrRCV_u = \frac{devRCV_u}{iRCV} = edrRCV_f \quad (25)$$

$$edrPV_u = \frac{devPV_u}{iPV}. \quad (26)$$

Now consider the case where the assumption that RCV is unchanged is not made. In this case the updated RCV is described in terms of the processes discussed in the three numbered assumptions above. Define $R_{internal}$ as the net change in red cell volume due to ongoing internal processes of red cell production and destruction, $R_{added}$ as the volume of red cells added via blood products, and $R_{lost}$ as the volume of red cell lost to bleeding.

$$\Delta RCV \equiv RCV_u - RCV_i$$

$$\Delta RCV = R_{internal} + R_{added} - R_{lost} \quad (27)$$

To the extent that $\Delta RCV$ can be quantified, one can generalize equations (18)-(20) to derive updated volume figures in terms of $pHct_u$ and $\Delta RCV$ as follows:

$$RCV_u = RCV_f + \Delta RCV \quad (28)$$

$$BV_u = \frac{RCV_f + \Delta RCV}{pHct_u * paf} \quad (29)$$

$$PV_u = (RCV_f + \Delta RCV) * \frac{(1 - pHct_u * paf)}{pHct_u * paf} \quad (30)$$

The equations for deviations (21)-(26) can now be used with these generalized values.

To what extent can the components of $\Delta RCV$ can be quantified with confidence? The applicability of an updated BVA measurement using $\Delta RCV$ depends on that confidence.

The $R_{added}$ component will generally be well knowable, as blood products are usually administered in discrete units. Then the added volume is simply the product of the number of units $N_{units}$ and the $RCV_{unit}$ of a single unit:

$$R_{added} = N_{units} * RCV_{unit} \quad (31)$$

For example, in the U.S., blood units are prepared from 500 ml of donor blood. The $RCV_{unit}$ would be 200 ml if the donor blood had a pHct of 40%, but this number could vary based on the possible acceptance range for donor blood, which is not the same everywhere, and varies for male and female donors. A fixed value such as 200 ml could be assumed for $RCV_{unit}$. A more precise value for a given patient could also be generated by measuring the actual volume of the units administered, either directly as they are infused, or indirectly by weighing the units, subtracting the weight of the packaging, and using an assumed value for the volume of red cells to the weight of packed cells. Such a ratio can be estimated from the typical 70% $Hct_{blood}$ of packed red cells, and the specific gravity of blood of 1.06 g/cm$^3$:

$$RCV_{unit} = (Weight_{unit} - Weight_{packaging}) * \frac{Hct_{blood}}{\text{specific } gravity_{blood}}. \quad (32)$$

Estimating $R_{lost}$ is sometimes done in the course of surgery, when blood loss is quantified via recaptured blood and/or weighing of absorbent materials. The accuracy of such measures, and of other clinical estimates of blood loss is a matter of clinical discretion. For stable patients who have not undergone surgery, it may be reasonable to assume $R_{lost}=0$.

Estimating $R_{internal}$ is most useful for short to moderate time intervals. Red blood cell production (erythropoiesis) takes place in the bone marrow and is moderated by the hormone erythropoietin (EPO), and is affected by numerous factors, particularly the availability of sufficient iron. Red blood cell lifetime is estimated to be 120 days, so an ongoing replacement level of both production and destruction could be assumed to be 1/120 of iRCV. Estimating the net internal change for a particular patient is a matter of clinical discretion, with uncertainty increasing approximately linearly with time. For follow-up periods significantly less than 120 days, it may be reasonable to assume $R_{internal}=0$.

The invention provides a system for automatically analyzing blood of a living patient, comprising a concentration counter configured to analyze the patient's blood, a user interface operatively connected to the concentration counter and configured for entry and display of information, a Hematocrit(Hct) monitor, and one or more processors operatively coupled to a memory and configured to execute programmed instructions stored in the memory to carry out a method comprising the steps of: a) gathering data from the concentration counter, related to the concentration of a tracer within the of blood of a patient, and from the Hct monitor; b) calculating, by the one or more processors, a blood volume (BV), plasma volume (PV), and red cell volume (RCV) for the patient; c) calculating, by the one or more processors, an ideal blood volume (iBV), ideal plasma volume (iPV), and red cell volume (iRCV) for the patient based on patient descriptive data such as height, weight, and gender; d) displaying, by the one or more processors, at the user interface, the results of steps (b) and (c); e) storing for later use the results of steps (b) and (c); f) measuring, at one or more later times, an updated value for patient Hematocrit (Hct); g) calculating, by the one or more processors, updated values for BV, PV, and RCV based on the updated Hct, without performing additional measurements related to the concentration of a tracer within the blood of the patient; and h) displaying, by the one or more processors, at the user interface, the results of step (g).

The Hct Monitor should be understood as any device or component capable of performing at least one measurement of Hct on the blood a living subject, either directly applied to the subject or to blood sampled from the subject. The mechanism of this measurement may take any form that results in an acceptably accurate measurement. Examples of such mechanisms include direct observation of the proportion of plasma and red cells in a spun sample of blood (such as in a microcentrifuge); measurement of concentrations of substances in the sample such as Hemoglobin that can be correlated and translated to a Hct measurement; measurement of blood flow directly in the living subject via Photoplethysmography (PPG) or other optical means, that can be correlated and translated to a Hct measurement.

The invention also provides such a system where step a) in [0029] involves the injection of a tracer into the patient prior to measuring (either in vivo or using collected in vitro samples) the concentration of the samples. The tracer used can be a radioactive isotope (for example I-131), or a light-emitting substance (such as fluorescent ICG or fluorescein) or light-absorbing (such as Evans blue dye).

The invention provides for the performance of step (g) in [0029] using the assumption that RCV is unchanged, and updated $BV_u$ and $PV_u$ values are calculated from the first $RCV_f$ value and the updated peripheral Hct value ($pHct_u$) and peripheral adjustment factor (paf), where paf takes on a constant value such as 0.9009:

$$RCV_u = RCV_f, BV_u = \frac{RCV_f}{pHct_u * paf},$$

-continued
$$PV_u = RCV_f * \frac{(1 - pHct_u * paf)}{pHct_u * paf}.$$

The invention provides for the performance of step (g) in [0029] using a value for the change in RCV (ΔRCV), and updated $BV_u$, $RCV_u$, and $PV_u$ values are calculated from the first $RCV_f$ value, $pHct_u$ and paf:

$$RCV_u = RCV_f + \Delta RCV, BV_u = \frac{RCV_f + \Delta RCV}{pHct_u * paf},$$

$$PV_u = (RCV_f + \Delta RCV) * \frac{(1 - pHct_u * paf)}{pHct_u * paf}.$$

The invention provides for the performance of step (g) in [0033] where ΔRCV is estimated according to the formula $\Delta RCV = R_{internal} + R_{added} - R_{lost}$.

The invention provides for the performance of step (g) in [0034] where $R_{added}$ is estimated based on the number and size of units of blood products administered.

The invention provides for the performance of step (g) in [0034] where $R_{lost}$ is estimated based on a measurement of blood loss during a medical procedure.

The invention provides for the system of [0029] where in addition treatment guidance is calculated based on the patient values, using protocol-derived rules stored within the system, and containing quantified patient-specific treatment information; and such guidance is displayed at the user interface by the one or more processors, based on the original BV calculation: after step (d), and based on the updated BV calculation after step (h). The treatment guidance may be presented in textual form, or in flow-chart form. The protocols for the system may be derived from one or more published protocols relating to blood volume management. Such protocols may be customizable by the user, to include one or more of the following features: alteration of thresholds for consideration of a treatment; addition of a treatment option; removal of a treatment option; alteration of the calculation for the quantity of a treatment, or alteration of the order of treatment options. The system may include one or more treatment capabilities that are connected to the system, such that quantified treatment can be administered to a patient by the system; such treatment may be automatic, or may require human approval at the time of, or before, administration. Such treatments may include: addition of saline or saline-equivalent fluids; addition of plasma or other oncotic-support fluids; addition of blood products such as packed red cells, whole blood, platelets, etc.; removal of fluids via dialysis or ultrafiltration; removal of red cells via erythrocytapheresis; manipulation of a drug (stopping/starting/adjusting dosage) that is connected to a patient via IV or oral means. The protocols may be customized to include other patient information besides BV, PV, RCV, iBV, iPV, and iRCV; such information may be entered by the user manually into the system or accessed via a network connection to the patient's medical records. The protocols may be customized to deal with specific patient conditions beyond the scope of simple volume management, but where knowledge of volume influences treatment decisions. Such conditions include Heart Failure, Syncope, Critical Care (including Sepsis and ARDS), Hypertension, and Renal Failure/Dialysis. An example of a heart failure protocol that deals with blood volume is the "2013 ACCF/AHA Guideline for the Management of Heart Failure" which states that "Volume status and vital signs should be assessed at each patient encounter." An example of a syncope protocol that deals with blood volume is the "2018 ESC Guidelines for the diagnosis and management of syncope" which contains extensive discussion of volume depletion as a possible cause of syncope. An example of a critical care protocol that deals with blood volume is the "The European guideline on management of major bleeding and coagulopathy following trauma: fourth edition" which contains extensive discussion of blood volume restoration, and includes percentage of blood volume loss in distinguishing the severity of hypovolemic shock (Class I-IV, as per the American College of Surgeons Advanced Trauma Life Support (ATLS) classification); each class is associated with differing treatment recommendations. An example of a hypertension protocol that deals with blood volume is the "2017 Guideline for the Prevention, Detection, Evaluation, and Management of High Blood Pressure in Adults: A report of the American College of Cardiology/American Heart Association Task Force on Clinical Practice Guidelines" which contains differential treatment recommendations based on the presence of volume depletion or volume overload. An example of a renal failure/dialysis protocol that deals with blood volume is the journal article "Blood volume analysis as a guide for dry weight determination in chronic hemodialysis patients: a crossover study" (Malha et al. *BMC Nephrology* 2019) which contains extensive discussion of the use of blood volume to obtain better outcomes.

The invention provides for the system of [0029] where the Hct monitor is located at a separate (remote) location to the concentration counter that performs step (a), and which connects with the rest of the system via data communications. The remote Hct monitor may take the form of: an integrated monitor and transceiver component; one Hct component which is connected to separate computing device (such as a computer, smartphone, smartwatch, tablet, etc.); one Hct component, where data communications with the rest of the system are handled by manual means (such as telephone, email, fax, etc.). The Hct monitor may be equipped with one or more processors, so as to receive or calculate updated results and guidance, and a display interface, to display results and guidance to a remote user. The Hct Monitor may be connected to one or more additional monitors, and the information from said monitors is considered in the calculation of guidance. Such additional monitors include: a Blood Pressure Monitor; a Glucose Monitor, whose measured Whole blood glucose may or may not be euvolemically corrected to Euvolemic plasma glucose; a Pulse Monitor; a Photo-plethysmography (PPG) Monitor; an Electro-Magnetic (EM) Monitor; a Blood Gas Monitor; a Comprehensive Blood Monitor. A monitor that has the capability of measuring Hct itself (such as a Comprehensive Blood Monitor or a PPG monitor) may be integrated as a Monitor and Transceiver offering additional guidance as well.

The invention provides for a method of analyzing the blood of a living patient, comprising: a) analyzing the blood of the patient with the system of [0029] to obtain a first patient blood volume measurement; and b) at one or more later times, measuring the patient Hct and using that value to calculate updated blood volume measurements without repeated concentration measurements. Step b) may be performed using the assumption that RCV is unchanged, and updated $BV_u$ and $PV_u$ values are calculated from the first $RCV_f$ value and the updated peripheral Hct value ($pHct_u$) and peripheral adjustment factor (paf), where paf takes on a constant value such as 0.9009:

$$RCV_u = RCV_f, \quad BV_u = \frac{RCV_f}{pHct_u * paf},$$

$$PV_u = RCV_f * \frac{(1 - pHct_u * paf)}{pHct_u * paf}.$$

Step b) may also be performed using a value for the change in RCV ($\Delta RCV$), and updated $BV_u$, $RCV_u$, and $PV_u$ values are calculated from the first $RCV_f$ value, $pHct_u$ and paf:

$$RCV_u = RCV_f + \Delta RCV, \quad BV_u = \frac{RCV_f + \Delta RCV}{pHct_u * paf},$$

$$PV_u = (RCV_f + \Delta RCV) * \frac{(1 - pHct_u * paf)}{pHct_u * paf}.$$

The value for $\Delta RCV$ may be estimated according to the formula $\Delta RCV = R_{internal} + R_{added} - R_{lost}$. The value for $R_{lost}$ may be estimated based on the number and size of units of blood products administered. The value for $R_{added}$ may be estimated based on a measurement of blood loss during a medical procedure.

The invention also provides for a method of analyzing the blood of a living patient, comprising: a) analyzing the blood of the patient with the system of [0037] to obtain a first patient blood volume measurement; and b) at one or more later times, measuring the patient Hct and using that value to calculate updated blood volume measurements without repeated concentration measurements, and provide treatment guidance.

The invention also provides for a method of analyzing the blood of a living patient, comprising: a) analyzing the blood of the patient with the system of [0038] that includes a remote monitor, to obtain a first patient blood volume measurement; and b) at one or more later times, measuring the patient Hct and using that value to calculate updated blood volume measurements without repeated concentration measurements.

FIG. 1 shows a preferred embodiment of the system. A blood volume analyzer with guidance (100), such as described in detail in U.S. Provisional Patent Application No. 62/753,174, performs a volume measurement (101) of patient XYZ (120). The analyzer produces an initial report including the patient's volume status and guidance (108), storing the record of the initial BV measurement (107) for use in calculating updated measurements. A Hct monitor (102) provides regular (or continuous) measurements of Hct, which are delivered to the analyzer. Various means of fluid intervention ("Blood/Fluids Controller" (103), "Drug Controller" (104), "Ultrafiltration Device" (105), "Erythrocytapheresis Device" (106)), shown with dotted outlines, are optionally connected to the patient; various interventions can be delivered to the patient based on the guidance produced by the analyzer. The clinician (121) enters changes to the patient's red cell mass that occur after the initial measurement is taken into the analyzer manually (122), when such changes occur as a result of interventions not performed by components connected to the analyzer. As examples of automated treatments, an erythrocytapheresis device may transmit to the analyzer a measure of the red cell volume that has been removed from the patient; the Blood/Fluids controller can communicate the volume of red cells delivered. As Hct information (102) and/or manual red cell information (122) changes, an updated report (123) is produced using information stored in the Patient XYZ record of Initial BV measurement (107), and shown to clinicians (121).

Figure 2:
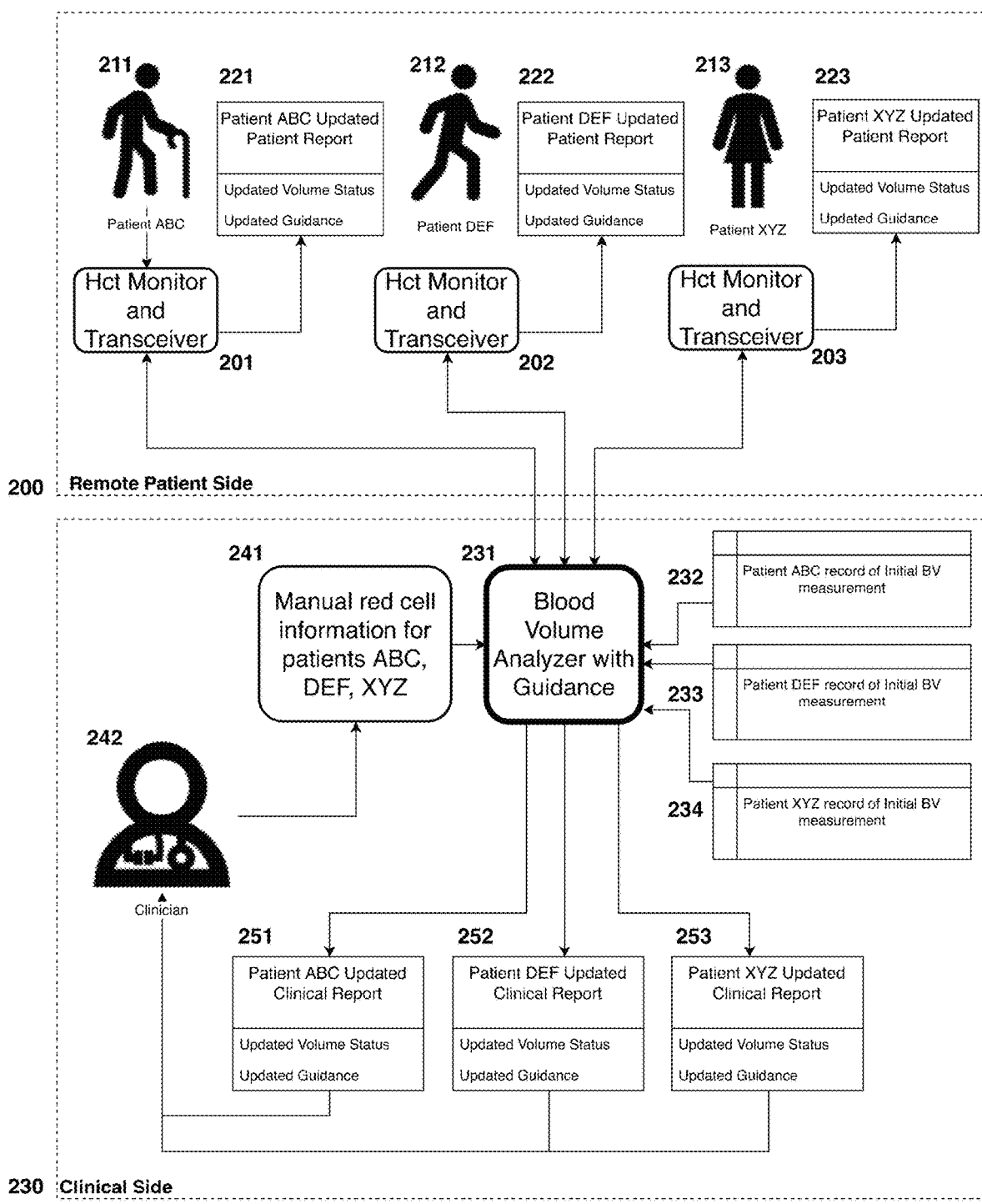
FIG. 2 shows a preferred embodiment of the system, in which remote monitoring is used to guide treatment for patients after an initial Blood Volume measurement.

FIG. 2 shows a preferred embodiment of the system, in which remote monitoring is used to guide treatment for patients after an initial Blood Volume measurement. On the "Remote Patient Side" (200) various patients (211-213) are depicted. Each patient has a Remote Hct Monitor and Transceceiver (201-203), which communicates with a Blood Volume Analyzer with Guidance (231), located on the "Clinical Side" (230), e.g. in a hospital or clinic. Each patient has previously had a BV measurement performed, and the results of these measurements (232-234) are stored by the analyzer. A clinician (242) manually enters information (241) about red-cell altering treatments the various patients may have received since their previous BV measurement. The analyzer calculates updated volume status and guidance, and provides updated reports and guidance (251-253) to the clinician. Additionally, each patient is provided with an updated report and guidance (221-223) of their personal status. In a preferred embodiment, the Remote Hct Monitor and Transceceiver (201-203) is capable of storing results of the original measurements (232-234) and of calculating and providing updated reports and guidance (221-223) to the patient without needing to communicate further with the analyzer (231).

Figure 3:
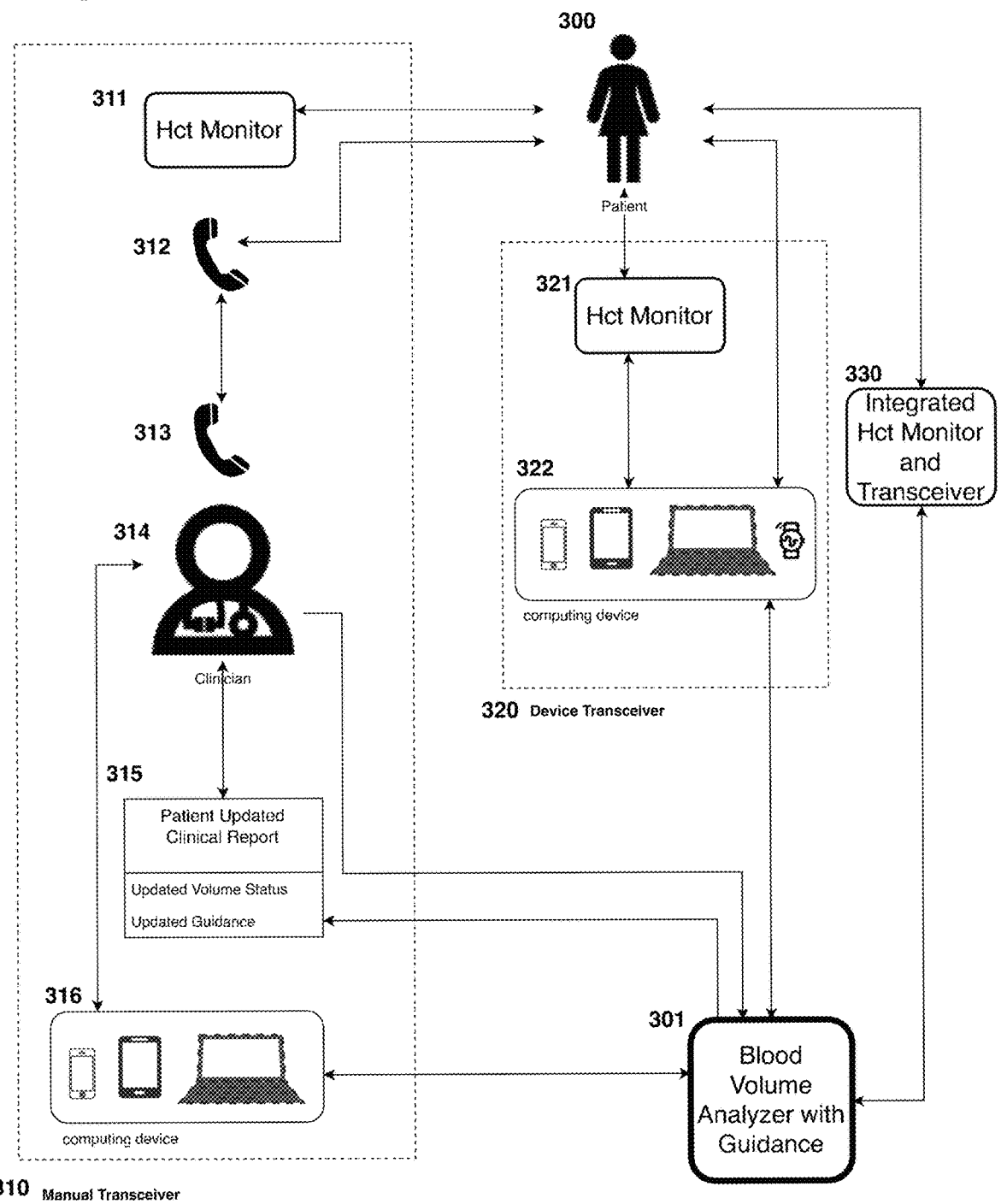
FIG. 3 shows details of various embodiments of the Hct Monitor and Transceiver, variously as an integrated device, or as comprised of various discrete elements.

FIG. 3 shows how the Remote Hct Monitor and Transceiver (201-203) depicted in FIG. 2 can take a variety of forms in various embodiments. A patient (300) is shown connected to a remote blood volume analyzer with guidance (301) by various means. In a preferred embodiment, an Integrated Hct Monitor and Transceiver (330) consists of a single autonomous unit comprising a Hct monitor component, a wireless data connection (such as Wifi or cellular capability), and a display; the unit can be worn on or attached to the body (e.g. as a smartwatch or strap) or be placed in contact with the body (e.g. a finger probe) or in contact with a sample of blood from the body. The monitor component measures the patient Hct; the wireless data connection component communicates with the remote analyzer, and the display presents information to the patient. The functioning of the transceiver in the larger system is shown in FIG. 2. In another embodiment, a Device Transceiver (320) consists of a local computing device (322) and a Hct monitor (321). The local computing device (a phone, smartwatch, tablet, laptop, computer, or other device) handles communications with the remote analyzer, using Wifi, cellular, or other data connection. The Hct monitor is connected to the data device using a wired connection, or a wireless connection (Bluetooth, Wifi, or other wireless connection), or via manual input of values from the monitor into the device. Updated results and guidance are conveyed to the patient via the display of the computing device or the Hct monitor. In another embodiment, a manual transceiver system (310) is shown. A Hct monitor (311) measures the Patient's Hct. The patient communicates the Hct value to the clinician (314) via a manual method (312→313) such as a telephone call, text message, email, fax, in-person clinical visit, etc. The clinician enters the updated Hct value into the analyzer (301), which produces an updated report (315) which is presented to the clinician. The clinician relays the updated report to the patient via the same or other manual means (313→312). In another embodiment of the Manual Transceiver (310), the Clinician (314) communicates with a remote Blood Volume Analyzer (301) using a computing device (316).

Figure 4:
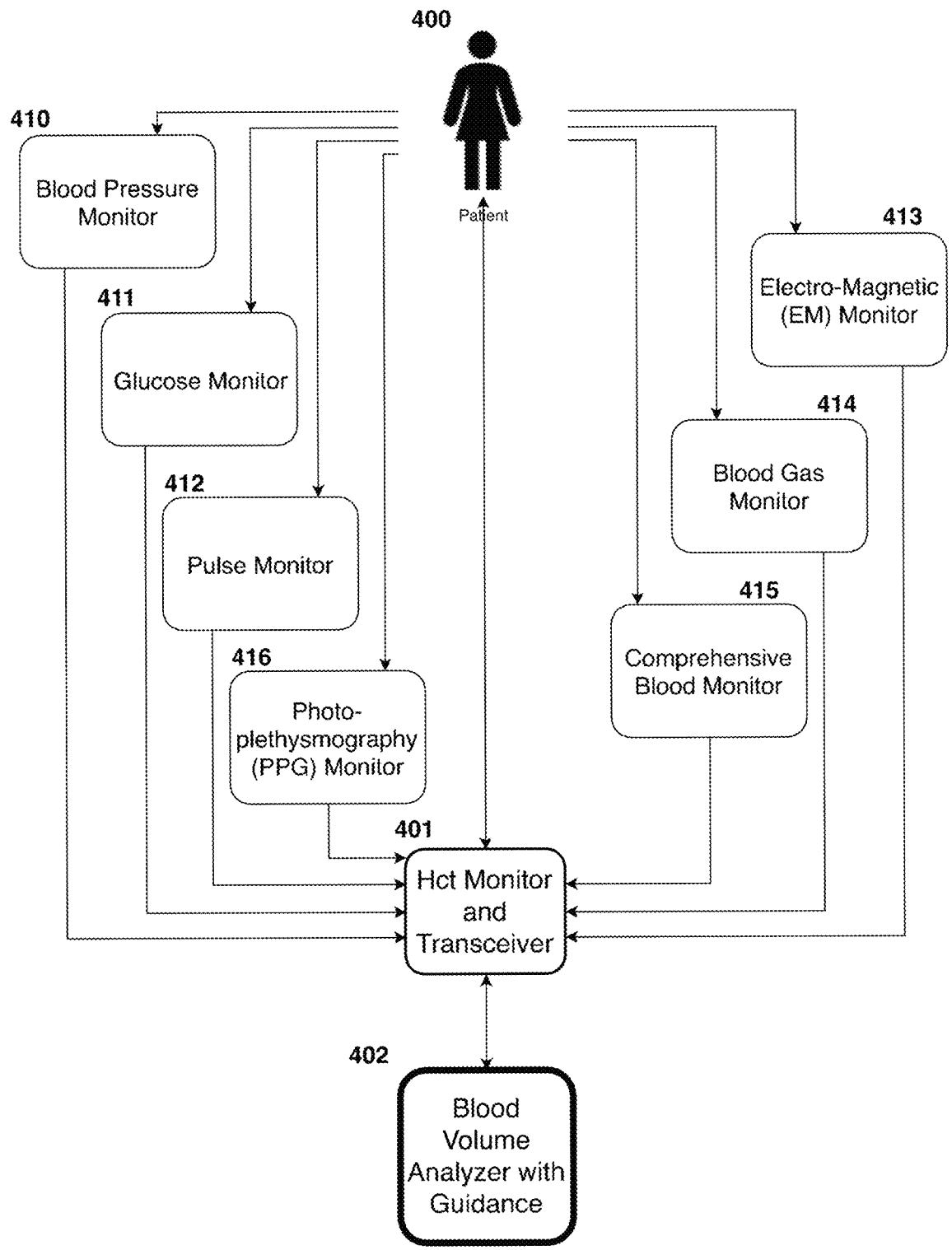
FIG. 4 shows various embodiments of a system which incorporates additional monitors which can supplement the Hct reading with additional patient data readings.

FIG. 4 shows how a Remote Hct Monitor and Transceiver (401) can be combined with other monitors in various embodiments. A patient (400) is shown connected to a remote blood volume analyzer with guidance (402) by means of a Hct Monitor and Transceiver (401). One or more additional monitors (410-416) are shown that may be connected to the transceiver, such that the data they provide is used to refine, alter, or supplement the guidance provided by the analyzer.

In one preferred embodiment, the Remote Hct Monitor and Transceiver is combined with a Blood Pressure Monitor (410). Many published guidelines for management of diverse conditions such as Heart Failure, Hypertension, and Syncope include thresholds for guided treatment using blood pressure (BP), and these same conditions have guidelines related to Blood Volume Measurement. A system or method that incorporates updated knowledge of both BP and blood volume can provide improved or more complete guidance than a system or method that relies on BP alone.

Similarly, in another embodiment, the Remote Hct Monitor and Transceiver is combined with a Pulse Monitor (412). A system or method that incorporates updated knowledge of both pulse and blood volume can provide improved or more complete guidance than a system or method that relies on pulse alone.

Similarly, in another embodiment, the Remote Hct Monitor and Transceiver is combined with a Photo-plethysmography (PPG) Monitor (416). This non-invasive technology uses visible light signals that are detected after being reflected through the skin from near-surface structures of a living being. PPG sensors are widely used in phones, smarts watches, and other smart wearable devices, and can be applied to various parts of the body such as fingers, ears, chest, mucous membranes, etc. The analysis of the PPG signal can be used to infer various circulatory measurements of interest in addition to Hct, such as pulse rate, respiration rate, cardiac stroke rate, peripheral oxygen saturation (SpO2), etc. A system or method that incorporates updated knowledge of both PPG-derived measurements and blood volume can provide improved or more complete guidance than a system or method that relies on PPG-derived measurements alone.

Similarly, in another preferred embodiment, the Remote Hct Monitor and Transceiver is combined with an Electro-Magnetic (EM) Monitor (413), for example one that is capable of revealing fluid in body cavities such as the lungs. A system or method that incorporates updated knowledge of both EM visualization and blood volume can provide improved or more complete guidance than a system or method that relies on EM visualization alone.

In another preferred embodiment, the Remote Hct Monitor and Transceiver is combined with a glucose monitor, and the glucose management is aided by the reporting of euvolemically corrected glucose values. As disclosed in application publication No. US2018/0217168A1, the euvolemic concentration of X (eX) that will be observed is changed by the ratio of V/iV, where V is the volume component that this being considered for purposes of concentration, and iV is the volume for that component after a correction to the ideal has been made:

$$eX = X * \frac{V}{iV} \quad (33)$$

where $$\frac{V}{iV} = \begin{cases} \frac{BV}{iBV} & \text{for whole blood concentration} \\ \frac{PV}{PV + (iBV - BV)} & \text{for plasma concentration} \end{cases} \quad (34)$$

The transceiver can display euvolemic whole blood glucose (eGlucose$_{wb}$), based on the whole blood glucose value Glucose$_{wb}$ generally calculated by patient glucose monitors (as opposed to the plasma glucose level Glucose$_{plasma}$ which is generally measures in labs, and which is most commonly used in guidelines and discussions about glucose management).

$$eGlucose_{wb} = Glucose_{wb} * \frac{BV}{iBV} \quad (35)$$

For glucose management, it is more desirable to display the euvolemic plasma glucose (eGlucose$_{plasma}$). If Glucose$_{plasma}$ is not measured directly, it is generally estimated by a plasma correction factor (plasma_cf), which is usually taken to be in the range 10%-12%:

$$Glucose_{plasma} = Glucose_{wb} * (1 + plasma_{cf}) \quad (36)$$

Then the euvolemic plasma glucose is:

$$eGlucose_{plasma} = Glucose_{plasma} * \frac{PV}{PV + (iBV - BV)} \quad (37)$$

corresponding to the plasma glucose level that would likely be observed if the patient's blood volume were corrected to a normal value. This euvolemic plasma glucose has the advantage of being a more accurate measure of the total measure of the sugar load of the bloodstream, as well as potentially providing insight into to the management of patients who have combined glucose and volume management needs—e.g. heart failure patients who also have diabetes, a not insignificant fraction.

In another preferred embodiment, a transceiver (401) is connected with a blood gas monitor (414) capable of performing an arterial blood gas (ABG) analysis. A typical analysis might contain measurements of pH, $PCO_2$, $PO_2$, $SO_2\%$, $HCO_3^-$, $SBC_e$, total $CO_2$, $O_2$ content, etc. Any values that are expressed as concentrations per unit volume can be presented as euvolemically corrected values. A system or method that incorporates updated knowledge of euvolemic ABG and blood volume can provide improved or more complete guidance than a system or method that relies on ABG alone.

A Comprehensive Blood Monitor (415) is a single device that includes monitoring or measuring capabilities for a wide variety of analytes, such as electrolytes, metabolites, coagulation, cardiac biomarkers, blood gases, hemoglobin, etc. Any values that are expressed as concentrations per unit volume can be presented as euvolemically corrected values. In a one embodiment, a transceiver (401) is connected with a Comprehensive Blood Monitor (415). As comprehensive blood monitors often include the capability of measuring Hct, in a preferred embodiment, the Comprehensive Blood Monitor (415) and Remote Hct Monitor and Transceiver (401) are integrated into a single device.

In various other embodiments, a transceiver (401) is connected with one or more additional monitors, drawn from the set described above (410-415) or other monitors that measure patient characteristics. For all of the embodiments derived from FIG. 4 discussed above, one skilled in the art would recognize that the connection of the additional monitors (410-415) to the transceiver (401) could take various forms ranging from integration into a single device, to piecewise connection such as is shown in FIG. 3.

Figure 5:
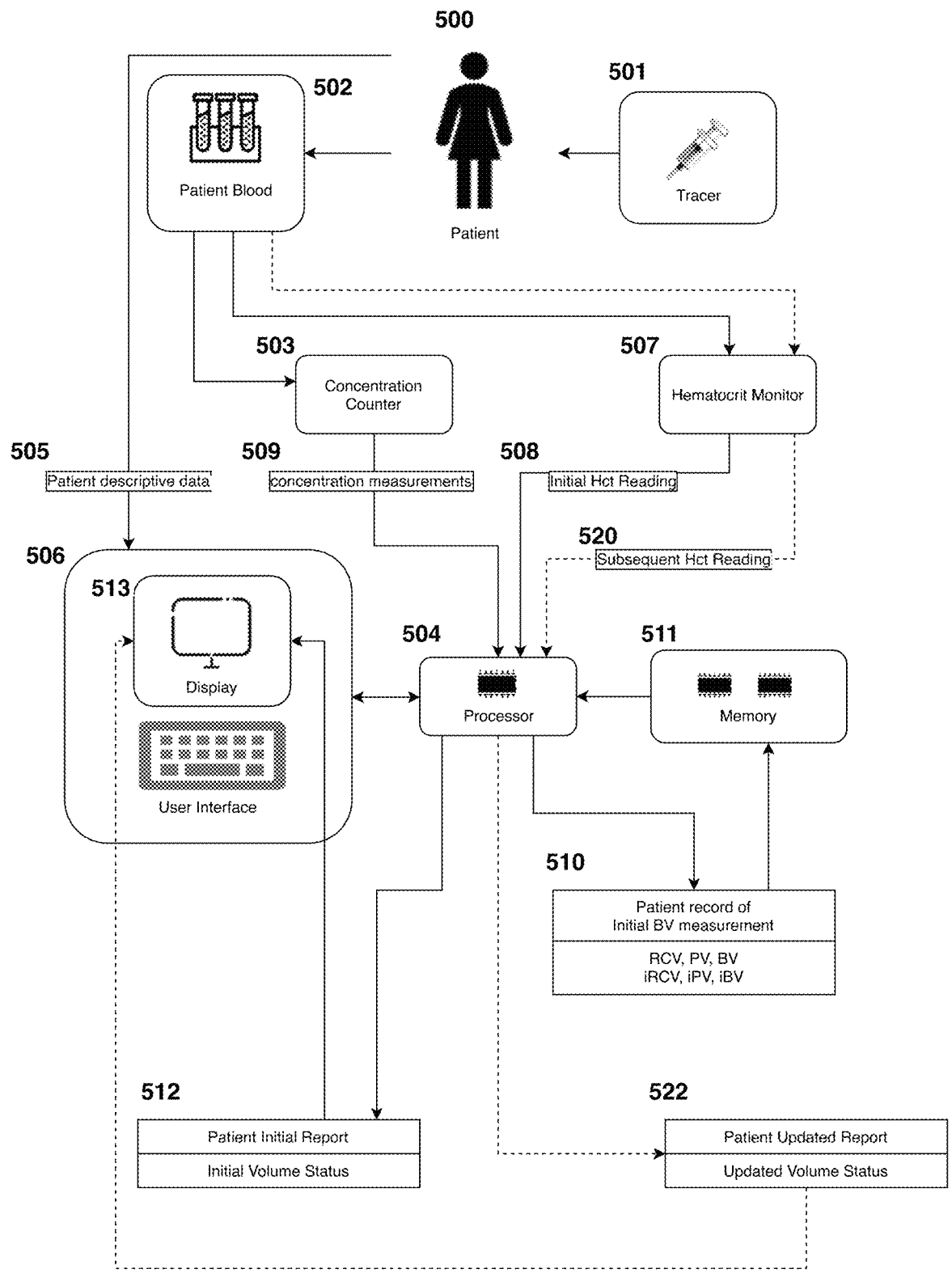
FIG. 5 shows an embodiment of a generic system in which a concentration counter measures the concentration of a tracer in a patient's blood at an initial time, and a Hct monitor measures patient Hct at an initial and subsequent time; these measurements are used to calculate and present an initial and updated report of patient blood volume status.

FIG. 5. shows an embodiment of the most generic system. A patient (500) is present whose blood (502) contains a measurable tracer (501). One or more of the measurements (509) of the concentration of tracer in the patient's blood are made at an initial time by a concentration counter (503), and the concentration measurements (509) are transmitted to a processor (504). Patient descriptive data such as height, weight, and gender (505) is entered via a user interface (506) connected to the processor. A Hematocrit monitor (507) measures an initial value for the patient Hct (508) and transmits this information to the processor (504). The processor uses this information (505, 508, 509) to calculate an initial blood volume measurement (510) which is stored in memory (511) that is connected to the processor. The processor prepares a report of the patient initial volume status (512) and presents it at the display element (513) of the user interface (506). At one or more subsequent times (depicted in FIG. 5 as dashed rather than solid connecting lines), a subsequent Hct reading (520) is made by the Hct monitor (507), without the need for addition concentration measurements. The processor (504) uses the subsequent Hct reading (520) in conjunction with the initial blood volume measurement information (510) which is stored in memory (511) to calculate a report of the patient updated volume status (522), which is then presented at the display element (513) of the user interface (506).

All combinations of the various elements described herein are within the scope of the invention unless otherwise indicated herein or otherwise clearly contradicted by context.

All publications, patents and patent application publications referred to herein are hereby incorporated by reference in their entirety into the subject application to more fully describe the art to which the subject invention pertains.

What is claimed is:

1. A system for automatically analyzing blood of a living patient, comprising
   a concentration counter configured to analyze the patient's blood,
   a Hematocrit(Hct) monitor,
   one or more processors operatively coupled to a memory, the concentration counter, and the Hct monitor,
   a user interface operatively connected to the one or more processors and configured for entry and display of information,
   where the one or more processors are configured to execute programmed instructions stored in the memory to carry out a method comprising the steps of:
   a. gathering or receiving data,
      i. from the concentration counter, related to the concentration of a tracer within the of blood of a patient, and
      ii. from the Hct monitor;

b. calculating, by the one or more processors, a blood volume (BV), plasma volume (PV), and red cell volume (RCV) for the patient based on data gathered or received in step (a);

c. calculating, by the one or more processors, an ideal blood volume (iBV), ideal plasma volume (iPV), and red cell volume (iRCV) for the patient based on patient descriptive data;

d. displaying, by the one or more processors, at the user interface, the results of steps (b) and (c);

e. storing for later use the results of steps (b) and (c);

f. measuring, at one or more later times, an updated value for patient Hematocrit (Hct);

g. calculating, by the one or more processors, updated values for BV, PV, and RCV based on the updated Hct, without performing additional measurements related to the concentration of a tracer within the blood of the patient; and h. displaying, by the one or more processors, at the user interface, the results of step (g).

2. The system of claim 1, where step (a.i) comprises:
1. Injecting a tracer into the bloodstream of the subject;
2. Collecting or observing blood samples from the subject over a time period after injection; and
3. Measuring the concentration of the tracer in the various samples.

3. The system of claim 1, where the tracer is a radioactive isotope, and the counter is a radiation counter equipped with one or more counting wells, with or without a mechanism for moving samples into counting wells.

4. The system of claim 1, where the tracer is a light-emitting (fluorescent) or light-absorbent (dye), and the counter is capable of measuring light emission or absorption either in one or more samples conveyed to the counter, or by direct measurement of circulating patient blood.

5. The system of claim 1, where step (g) is performed using the assumption that RCV is unchanged, and updated $BV_u$ and $PV_u$ values are calculated from the first $RCV_f$ value and the updated peripheral Hct value ($pHct_u$) and peripheral adjustment factor (paf), where paf takes on a constant value: $RCV_u = RCV_f$, $$RCV_u = RCV_f, BV_u = \frac{RCV_f}{pHct_u * paf},$$
$$PV_u = RCV_f * \frac{(1 - pHct_u * paf)}{pHct_u * paf}.$$

6. The system of claim 5, wherein paf takes on a constant value of 0.9009.

7. The system of claim 1, where step (g) is performed using a value for the change in RCV (ΔRCV), and updated $BV_u$, $RCV_u$, and $PV_u$ values are calculated from the first $RCV_f$ value, $pHct_u$ and paf:

$$RCV_u = RCV_f + \Delta RCV, BV_u = \frac{RCV_f + \Delta RCV}{pHct_u * paf},$$
$$PV_u = (RCV_f + \Delta RCV) * \frac{(1 - pHct_u * paf)}{pHct_u * paf}.$$

8. The system of claim 7, where ΔRCV is estimated according to the formula $\Delta RCV = R_{internal} + R_{added} - R_{lost}$.

9. The system of claim 8, where $R_{added}$ is estimated based on the number and size of units of blood products administered.

10. The system of claim 8, where $R_{lost}$ is estimated based on a measurement of blood loss during a medical procedure.

11. The system of claim 1, where treatment guidance is calculated based on the patient values, using protocol-derived rules stored within the system, and containing quantified patient-specific treatment information; and such guidance is displayed at the user interface by the one or more processors, based on the original BV calculation:
a. after step (d), and
b. based on the updated BV calculation after step (h).

12. The system of claim 11, wherein one or more treatment capabilities are connected to the system, such that quantified treatment can be administered to a patient by the system.

13. The system of claim 11, where one of the treatments is one or more of
a. addition of saline or saline-equivalent fluids, plasma or other oncotic-support fluids
b. removal of fluids via dialysis or ultrafiltration
c. addition of blood products
d. removal of red cells via erythrocytapheresis
e. removal of whole blood via therapeutic phlebotomy
f. manipulation of a drug (stopping/starting/adjusting dosage) that is connected to a patient via IV, oral, respiratory, or other means.

14. The system of claim 13, wherein the blood products comprise one of more of packed red cells, whole blood, and platelets.

15. The system of claim 11, where the protocols in step (d) are customized to deal with specific patient conditions beyond the scope of simple volume management, and where zero or more items of patient information beyond volume status are considered.

16. The system of claim 15, where the conditions are is one or more of the following conditions:
a. Heart Failure
b. Syncope
c. Critical Care
d. Hypertension
e. Renal Failure/Dialysis
f. Burns
g. Sepsis
h. Acute Respiratory Distress Syndrome
i. Surgical Blood Loss
j. Hyponatremia.

17. The system of claim 1, where the Hct monitor is located at a separate location to the concentration counter that performs step (a), and which connects with the rest of the system via data communications, where such data communications are handled by a dedicated transceiver incorporated into the Hct monitor, or by a separate computing device, or by manual means, or some combination thereof.

18. The system of claim 17, where the Hct monitor is equipped with one or more processors, so as to receive or calculate updated results and guidance, and a display interface, to display results and guidance to a remote user.

19. The system of claim 17, where the Hct Monitor is operatively connected to one or more additional monitors, and the information from said monitors is considered in the calculation of guidance.

20. The system of claim 19, where values that are measured in units of concentration are euvolemically corrected to display concentrations in terms of ideal patient volume.

21. The system of claim 19, where one or more of the additional monitors is one or more of the following:
   a. Blood Pressure Monitor
   b. Glucose Monitor
   c. Pulse Monitor
   d. Photo-plethysmography (PPG) Monitor
   e. Electro-Magnetic (EM) Monitor
   f. Blood Gas Monitor
   g. Comprehensive Blood Monitor.

22. The system of claim 21, where one of the additional monitors is a glucose monitor and measured whole blood glucose concentration is euvolemically corrected to euvolemic plasma glucose concentration.

23. The system of claim 17, wherein the separate computing device comprises one or more of a computer, smartphone, smartwatch, and tablet.

24. The system of claim 17, wherein the manual means comprises one or more of a telephone, email, and fax.

25. A method of analyzing the blood of a living patient, comprising:
   a. analyzing the blood of the patient with the system of claim 1 to obtain a first patient blood volume measurement; and
   b. at one or more later times, measuring the patient Hct and using that value to calculate updated blood volume measurements without repeated concentration measurements.

26. The method of claim 25, where step (b) is performed using the assumption that RCV is unchanged, and updated $BV_u$ and $PV_u$ values are calculated from the first $RCV_f$ value and the updated peripheral Hct value ($pHct_u$) and peripheral adjustment factor (paf), where paf takes on a constant value $$RCV_u = RCV_f, \; BV_u = \frac{RCV_f}{pHct_u * paf},$$

$$PV_u = RCV_f * \frac{(1 - pHct_u * paf)}{pHct_u * paf}.$$

27. The method of claim 26, wherein paf takes on a constant value of 0.9009.

28. The method of claim 25, where step (b) is performed using a value for the change in RCV ($\Delta RCV$), and updated $BV_u$, $RCV_u$, and $PV_u$ values are calculated from the first $RCV_f$ value, $pHct_u$ and paf $$RCV_u = RCV_f + \Delta RCV, \; BV_u = \frac{RCV_f + \Delta RCV}{pHct_u * paf},$$

$$PV_u = (RCV_f + \Delta RCV) * \frac{(1 - pHct_u * paf)}{pHct_u * paf}.$$

29. The method of claim 25, where the updated measurement of Hct is performed at a separate location to the location of the initial BV measurement.

30. The method of claim 25, where treatment guidance is provided based on an initial or updated blood volume measurement, using protocol-derived rules, and containing quantified patient-specific treatment information and alerts.

31. The method of claim 30, where treatment guidance is provided for one or more of the following conditions:
   a. Heart Failure
   b. Syncope
   c. Critical Care
   d. Hypertension
   e. Renal Failure/Dialysis
   f. Burns
   g. Sepsis
   h. Acute Respiratory Distress Syndrome
   i. Surgical Blood Loss
   j. Hyponatremia.

32. The method of claim 30, where information from one or more additional monitors is considered in the calculation of guidance.

33. The method of claim 32, where one or more of the additional monitors is one or more of the following:
   a. Blood Pressure Monitor
   b. Glucose Monitor
   c. Pulse Monitor
   d. Photo-plethysmography (PPG) Monitor
   e. Electro-Magnetic (EM) Monitor
   f. Blood Gas Monitor
   g. Comprehensive Blood Monitor.

34. The method of claim 32, where values that are measured in units of concentration are euvolemically corrected to concentrations in terms of ideal patient volume.

35. The system of claim 1, wherein the patient descriptive data comprise one or more of the patient's height, weight, and gender.

* * * * *